United States Patent [19]

Vieira

[11] Patent Number: Plant 6,118

[45] Date of Patent: Mar. 1, 1988

[54] PLUM TREE, "BROKEN HEART"

[75] Inventor: Frank A. Vieira, Visalia, Calif.

[73] Assignees: Livorio C. Huerta; Elsie E. Huerta, both of Reedley, Calif.

[21] Appl. No.: 812,358

[22] Filed: Dec. 23, 1985

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is somewhat similar to the Elephant Heart Plum Tree (unpatented) from which it is a scaffold mutation but which is distinguished therefrom by having a greenish-yellow skin color, a prominent suture line, and a unique, attractive orangish-yellow flesh having red striations which extend from the pit cavity to an area adjacent to the skin surface and which is further aromatic and of excellent eating quality.

1 Drawing Figure

BACKGROUND OF THE NEW VARIETY

The present invention relates to a new and distinct variety of plum tree, designated varietally as the "Broken Heart", and more particularly to a plum tree which bears fruit ripe for harvesting from approximately August 6 through August 16 at Visalia, Calif. and which is most closely related to the Elephant Heart Plum Tree (unpatented) from which it is a single scaffold mutation, but from which it is distinguished by producing a plum having a greenish-yellow external coloration and a pronounced reddish colored suture line, and by its unique and attractive yellowish-orange flesh which has red striations which radiate from the pit cavity outwardly towards the skin surface of the fruit.

For many years, the inventor has been engaged in farming at his fruit orchard at 31827 Road 148, Visalia, Calif. In early 1960, the inventor planted approximately eight acres of Elephant Heart Plum Trees (unpatented). During routine orchard operations in the fall of 1978, the inventor observed in a cultivated area one of the Elephant Heart Plum Trees having a limb that bore a greenish-yellow fruit. The limb was marked and thereafter observed during successive years. When the unique qualities of the subject variety were recognized, the applicant asexually reproduced the new variety by removing bud wood from the single scaffold mutation and budding both peach and Marianna plum rootstock. This first asexual reproduction was accomplished in the spring of 1979. The newly budded trees produced their first fruit in 1982. The budded test trees have subsequently been observed for the years 1983, 1984 and 1985 and it has been determined that the newly budded trees dependably and accurately reproduced fruit of superior characteristics observed by the inventor in the original scaffold mutation.

The instant variety is distinguishable from the Elephant Heart Plum (unpatented) by its greenish-yellow skin color and its quite attractive yellowish-orange flesh which has red striations throughout, which extend radially from the pit cavity outwardly toward the skin, and by its excellent eating qualities.

BRIEF DESCRIPTION OF THE DRAWING

The accompanying drawing is a color photograph of a characteristic twig bearing typical leaves, a cluster of plums showing their external coloration sufficiently matured for harvesting and shipment, several of the plums when matured on the tree, a plum halved transversely of the suture plane to illustrate the flesh coloration, and several stones, all of the subject variety.

DETAILED DESCRIPTION

Referring more specifically to the pomological details of this new and distinct variety of plum tree, the following has been observed under the ecological conditions prevailing in the designated orchard near Visalia, Calif. All major color code designations are by reference to the Maerz and Paul Dictionary of Color published in 1950. Common descriptive color names are also used occasionally.

TREE

Size: Medium to large, depending upon pruning practices.

Vigor: Vigorous; hearty under the agricultural conditions existing in the San Joaquin Valley of central California.

Figure: Variable; upright, spreading, usually trained to open vase form.

Productivity: Productive.

Regularity of bearing: Regular.

Trunk:

- *Thickness.*—Average.
- *Texture of bark.*—Rough.
- *Color.*—Brownish gray, (7-C-11) to (7-C-9).
- *Lenticels — Numbers.*—Numerous.
- *Lenticels — Size.*—Medium to large.

Branches:

- *Thickness.*—Average.
- *Texture.*—Medium.
- *Color — Mature branches.*—Brownish-gray, approximately (7-C-9).
- *Color — Immature branches.*—Green, (20-G-7).
- *Lenticels — Numbers.*—Numerous.

LEAVES

Size: Moderately large.

Length: Approximately 14.2 cm.

Width: Approximately 6 cm.

Thickness: Average for the species.

Form: Oval; the blade appears flat and is slightly reverse folded; leaf tip acuminate.

Texture: Slightly rugose.

Color:

*Dorsal surface.*—Dark-green, approximately (23-L-8).

*Ventral surface.*—Grayish-green, approximately (21-E-4).

Marginal form: A dull serrate along the basal shoulder, changing to crenate from the mid leaf portion to the apex; occasionally, leaves may be found that display a form being doubly crenate and somewhat irregular along the apical shoulder; margin is moderately undulate.

Petiole: Moderately long, approximately 13 to 16 mm. in length.

*Thickness.*—Approximately 2 mm.

*Color.*—Greenish-yellow, approximately (20-D-2).

Stem glands:

*Size.*—Large.

*Form.*—Mixed; however they appear most often in reniform.

*Numbers.*—They appear most often in groups of four although occasionally, numbers from two to five may also be found.

*Position.*—Alternate.

*Color.*—Orange-yellow when young, (10-J-6); glands will turn brown with age.

*Other characteristics.*—Glands are most often borne on the petiole itself, and are less frequently found at the base of the leaf blade.

Stipules:

*Size.*—Medium.

*Location.*—At the base near the petiole.

*Color.*—Light-green, approximately (17-H-5); this color will darken with age; early deciduous.

FRUIT

Maturity when described:

*Ripe for harvesting.*—August 6 through August 16 at Visalia, Calif.

*Size.*—Large.

*Axial diameter.*—Approximately 58 mm.

*Diameter transverse in the cheek plane.*—Approximately 57.7 mm.

*Diameter transverse in suture plane.*—Approximately 57 mm.

*Uniformity.*—Uniform.

Form: Broadly cordate, symmetrical; nearly globose in apical aspect.

Suture: A very distinct purplish-red line extending from the base to the apex; approximately 2 through 2.5 mm. in width at mid suture; the suture narrows basally and apically.

*Color.*—Purplish-red, approximately (6-H-4); the suture color is in stark contrast to the greenish-yellow coloration of the skin, (infra).

Ventral surface: Rounded; smooth with practically no lips; sides symmetrical.

Stem cavity:

*Depth.*—Medium, approximately 10 to 11 mm.; rounded, oval; and narrow.

*Width.*—Approximately 16 to 20 mm.

*Length.*—Approximately 18 to 21 mm.

Base: Rounded to very slightly truncate; the base is frequently at substantially right angles to the various axes of the fruit.

Apex: Moderately prolonged.

Pistil point: Apical.

Stem:

*Length.*—Medium, approximately 11 to 14 mm.

*Thickness.*—Approximately 1.5 through 2.5 mm.

*Color.*—Yellowish-green to brown, approximately (17-G-4) to (7-E-10).

Skin:

*Thickness.*—Medium; slightly acidic; tenacious to flesh; no observed tendency to crack; smooth surface texture.

*Color.*—Greenish-yellow approximately (12-L-2) to (12-L-4); a moderate amount of skin checking, especially in the area of the basal shoulder and inside the stem cavity has been observed.

*Lenticels — Number.*—Numerous very fine white lenticels have been observed over the entire surface of the fruit.

*Bloom.*—Skin surface is covered with a heavy gray bloom.

Flesh:

*Color.*—Variable; from a yellowish-orange near the skin surface to a lighter orange in and around the pit cavity, approximately (10-H-8) to (10-E-6), respectively; some slight greenish coloration is evident in an area approximately 2 to 3 mm. from the skin's surface; the flesh displays rays of bright red coloration which extends radially through the yellow-orange flesh from the pit cavity to just adjacent to the skin surface, approximately (5-L-10); the amount of red striations is somewhat variable from fruit to fruit but without exception the striations are present to some degree; in the case of the suture plane, the red striations extend from the pit cavity through to the surface of the skin causing the suture line to be quite prominent.

*Texture.*—Firm, meaty, and becoming quite juicy with maturity.

*Fibers.*—Long yellow fibers are evident upon inspection of the flesh; Numbers — average; tender.

*Ripening.*—Even.

*Flavor.*—Noteworthy, having a balanced, rich flavor.

*Aroma.*—Variable, slight to moderate.

*Eating quality.*—Excellent.

Stone:

*Free or cling.*—Semi-free; the stone is tightly formed in the pit cavity but breaks free relatively easily except along the ventral suture and occasionally around the apex.

*Other characteristics.*—Flesh pocket may occasionally form in the area of the apex, some internal gumming has been observed within this flesh pocket.

*Stone size.*—Medium.

*Length.*—Approximately 24.8 mm.

*Width.*—Approximately 17.2 mm.

*Thickness.*—Approximately 11.2 mm.

*Fibers.*—Short.

*Form.*—Narrowly ovate.

*Base.*—Rounded to very slightly truncate; the base of the stone is at right angles to the stone axis.

*Hilum.*—Narrow, oval and small.

*Apex.*—Acute.

*Size.*—Somewhat slightly unequal.

*Stone surface.*—Texture — relatively smooth, however the surface texture is slightly roughened over the apical shoulders.

*Ventral edge.*—A low wing is evident from the apex to mid suture, occasionally it extends to the base, one large groove is present below, and parallel to, the suture on each side of the stone, this groove extends from the apex to the base; some pits examined have evidence of occlusions along the ventral surface.

*Dorsal edge.*—A deep groove extends from the base, to approximately 5 to 7 mm. above the base; the mid-suture area appears smooth, although occasionally deep pits are evident; a narrow groove extends from the apex to an area approximately 7 to 9 mm. below the apex.

*Stone color.*—(9-H-4).

*Tendency to split.*—None observed.

Use: Fresh market.

Keeping quality: Good.

Resistance to disease and insects: No particular susceptibilities noted.

Shipping qualities: Unknown.

Although the new variety of plum tree possesses the described characteristics as a result of the growing conditions prevailing in Visalia, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described which is somewhat similar to the Elephant Heart Plum Tree (unpatented) from which it is a scaffold mutation, but from which it is distinguished by bearing fruit which is greenish-yellow in external coloration with a pronounced purplish-red suture line, and by its unique orangish-yellow flesh which has red colored striations that extend radially from the pit cavity to an area just adjacent to the surface and which is further ripe for harvesting approximately August 6 through August 16 at Visalia, Calif.

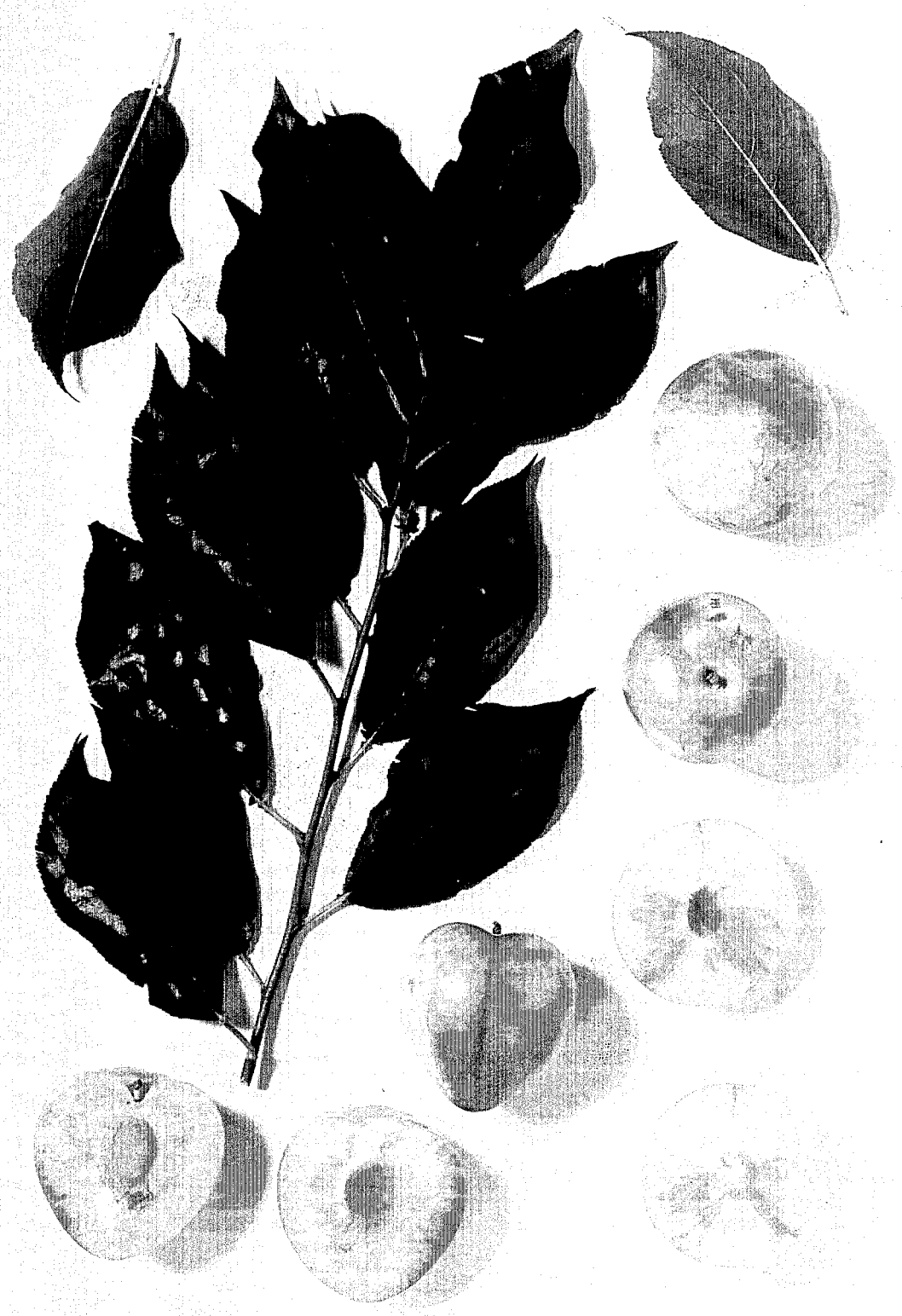

* * * * *